(12) United States Patent
Perryman et al.

(10) Patent No.: US 11,832,854 B2
(45) Date of Patent: Dec. 5, 2023

(54) LAMINOPLASTY HINGES

(71) Applicant: Choice Spine, LLC, Knoxville, TN (US)

(72) Inventors: John Abe Perryman, Columbia, TN (US); Larry T. Khoo, Studio City, CA (US)

(73) Assignee: Choice Spine, LLC, Knoxville, TN (US)

( * ) Notice: Subject to any disclaimer, the term of this patent is extended or adjusted under 35 U.S.C. 154(b) by 385 days.

(21) Appl. No.: 17/093,910

(22) Filed: Nov. 10, 2020

(65) Prior Publication Data
US 2022/0015808 A1 Jan. 20, 2022

Related U.S. Application Data

(63) Continuation of application No. 16/106,422, filed on Aug. 21, 2018, now Pat. No. 10,869,698.

(60) Provisional application No. 62/558,957, filed on Sep. 15, 2017.

(51) Int. Cl.
| | |
|---|---|
| *A61B 17/70* | (2006.01) |
| *A61B 17/88* | (2006.01) |
| *A61B 90/00* | (2016.01) |
| *A61F 2/30* | (2006.01) |

(52) U.S. Cl.
CPC ...... *A61B 17/7071* (2013.01); *A61B 17/8858* (2013.01); *A61B 2090/037* (2016.02); *A61F 2002/30471* (2013.01)

(58) Field of Classification Search
CPC ............. A61B 17/7071; A61B 17/8858; A61F 2002/30471
USPC .................................................. 606/246–249
See application file for complete search history.

(56) References Cited

U.S. PATENT DOCUMENTS

| | | | |
|---|---|---|---|
| 8,926,664 B1* | 1/2015 | Millhouse | A61B 17/8009 623/17.11 |
| 2008/0234739 A1* | 9/2008 | Hudgins | A61B 17/7026 606/255 |
| 2012/0271359 A1* | 10/2012 | Stevenson | A61B 17/808 606/280 |
| 2013/0060283 A1* | 3/2013 | Suh | A61B 17/7007 606/246 |

\* cited by examiner

*Primary Examiner* — Eduardo C Robert
*Assistant Examiner* — Tara Rose E Carter
(74) *Attorney, Agent, or Firm* — Luedeka Neely, P.C.

(57) ABSTRACT

A surgical implant device configured to adjust in planar orientation or angular orientation or both to correspond to the structure of the lamina to be spanned at the site of a cut of the laminoplasty surgery. The device includes a base having slots extending adjacent thereto, and an extension having a head configured to be adjustably positionable within the slots.

13 Claims, 12 Drawing Sheets

LAMINOPLASTY HINGES

CROSS-REFERENCE TO RELATED APPLICATION

This application is a continuation of U.S. application Ser. No. 16/106,422 filed Aug. 21, 2018, entitled LAMINOPLASTY HINGES (allowed), which claims priority to US Provisional Application No. 62/558,957 filed Sep. 15, 2017, entitled LAMINOPLASTY HINGES, incorporated herein by reference in their entireties.

FIELD

This disclosure relates to the field of laminoplasty surgery. More particularly, this disclosure relates to hinge structures and the use thereof in laminoplasty surgery.

BACKGROUND

Improvement is desired in devices for use in laminoplasty surgery. Laminoplasty is a spine surgery procedure in which the lamina at the posterior of the spine is removed. One type of laminoplasty referred to as Open Door Laminoplasty involves making two cuts to relieve pressure on the spine. One cut is made completely through one side of the vertebrae between the lamina and lateral mass. A second partial cut is made on the opposite lateral side. The lamina is hinged about the partial cut. Implant devices are often affixed to the spine at the locations of the cuts to provide support.

The present disclosure relates to improved devices for use in laminoplasty procedures, and particularly for use with open door laminoplasty procedures. The devices are advantageously configured to be able to adjust in planar orientation or angular orientation or both. This advantageously enables a reduction in the inventory of device sizes and enables the device to be adjusted in size. The ability to adjust the angular orientation of the device enables the device to be oriented to lie flush with on the lamina without having to bend the material of the device as is done conventionally.

SUMMARY

The above and other needs are met by surgical implant devices. The implant devices are desirably configured for use at complete cut and partial cut locations of an open door laminoplasty surgical site.

The surgical implant devices are configured to be adjustable in size and orientation so as to be adaptable to a surgical site.

In one aspect, a surgical implant device according to the disclosure includes a base and an extension adjustably connectable to the base to enable adjustment of both planar and angular orientations of the surgical implant device. The base has a seat and a back extending from the seat.

The extension has an elongated body with a head at an end of the elongated body of the extension, the head having oppositely extending arms. The head of the elongated body of the extension is positionable between the slots of the base so that the arms of the head of the elongated body span between the slots of the back of the base, When the head of the extension is positioned between the slots of the base when the implant device is installed in a patient during surgery, the head of the extension is freely pivotable within the slots of the base to permit a plurality of angular orientations of the implant device. Also, the head is movable along the elongate length of the slots to provide adjustment of the planar orientation of the implant device based on the location of the head along the elongate length of the slots.

In another aspect, there is provided a surgical implant device surgical implant configured to be adjustable in size and orientation so as to be adaptable to a surgical site. The implant device includes a base and an extension adjustably connectable to the base to enable adjustment of both planar and angular orientation of the surgical implant device.

The base has a seat and a back extending from the seat. The extension has an elongated body with a head at an end of the elongated body of the extension. The head is pivotally mountable or movably mountable or both to the extension to permit a plurality of different configurations of the implant device.

In a further aspect, there is provided a surgical implant device configured for use at the complete cut location of an open door laminoplasty surgical site to span between a lamina of a vertebrae and an open mass of a vertebrae, the implant device configured to be adjustable in size and orientation so as to be adaptable to the open door laminoplasty surgical site at the time of surgery.

The implant device includes a base and an extension adjustably connected to the base to enable adjustment of planar orientation or angular orientation or both of the surgical implant device.

The base has a seat and a back extending from the seat in a reclined relationship, a pair of spaced apart and aligned elongate slots located at a distal end of the back of the base, a hook configured to be able to hook onto the lamina of the vertebrae and a foot configured to be able to buttress against the lateral mass of the vertebrae.

The extension has an elongated body with a head at an end of the elongated body of the extension. The head has oppositely extending arms. The head of the elongated body of the extension is positionable between the slots of the base so that the arms of the head of the elongated body span between the slots of the back of the base.

When the head of the extension is positioned between the slots of the base when the implant device is installed in a patient during surgery, the head of the extension is freely pivotable within the slots of the base to permit a plurality of angular orientations of the implant device and the head is movable along the elongate length of the slots to provide adjustable planar orientation of the implant device based on the location of the head along the elongate length of the slots.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
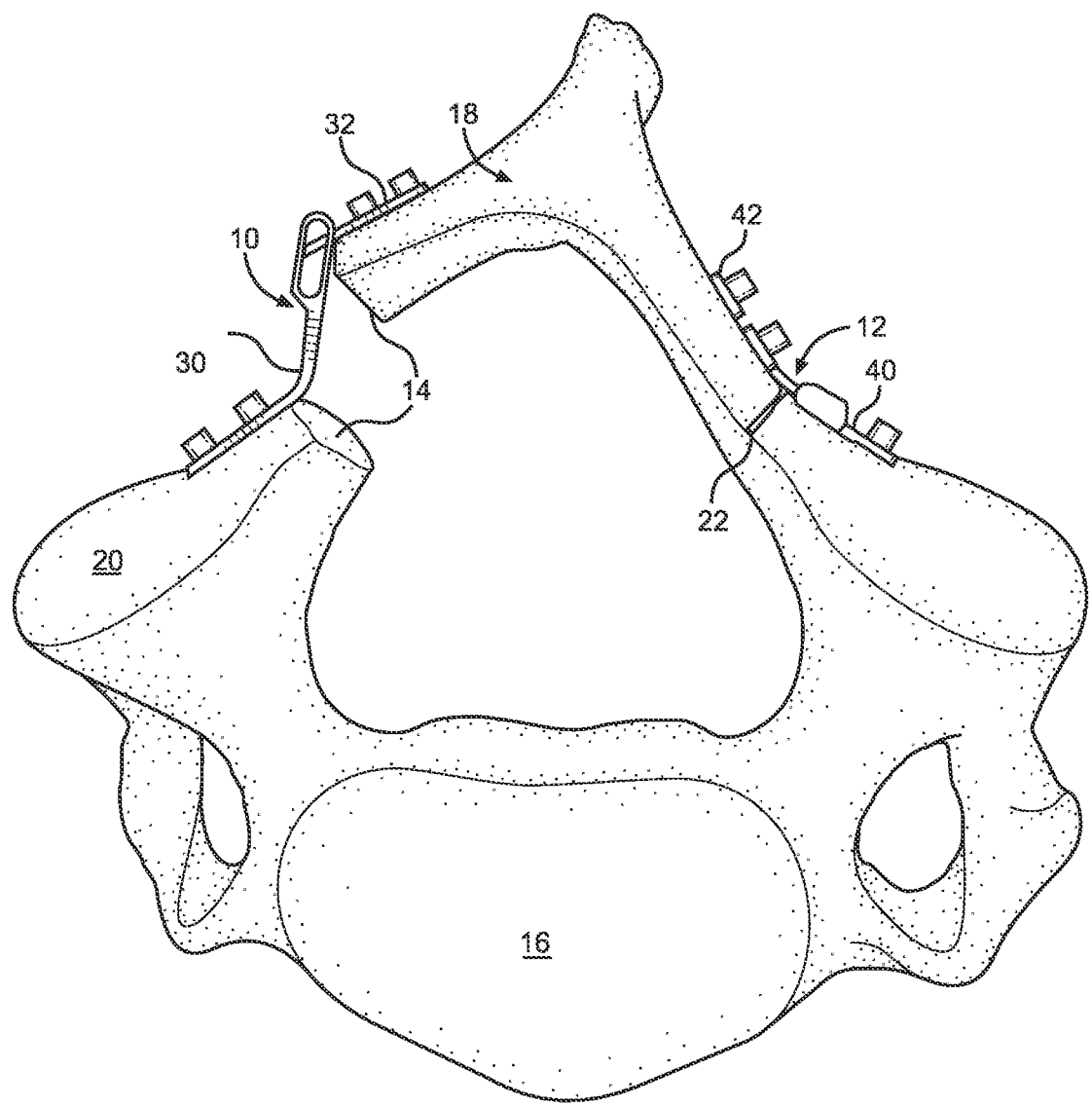
FIGS. 1-3 depict use of devices according to the disclosure as used for an open door laminoplasty procedure.
Figure 2:
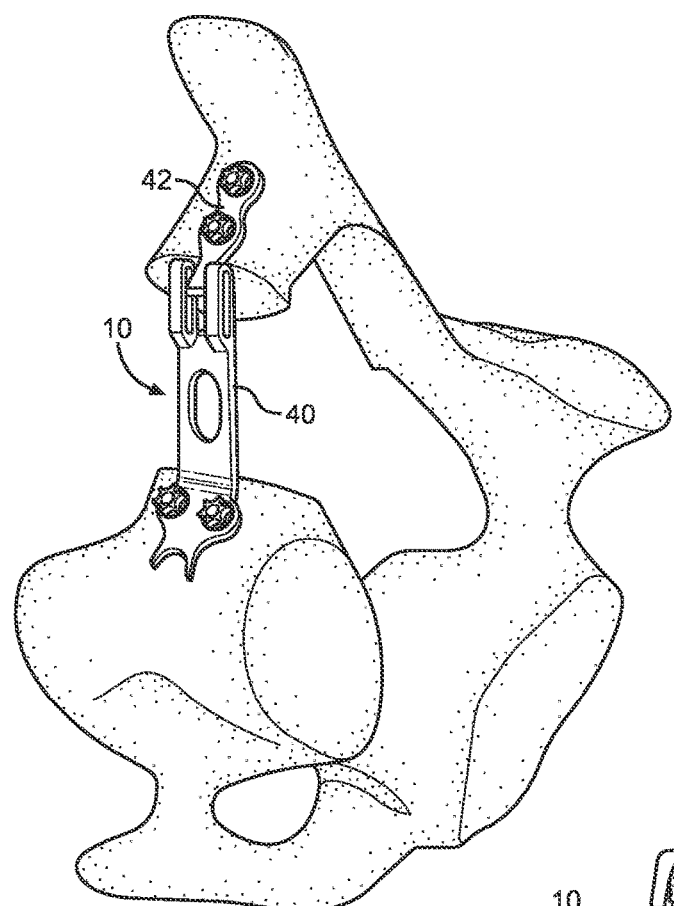
Figure 3:
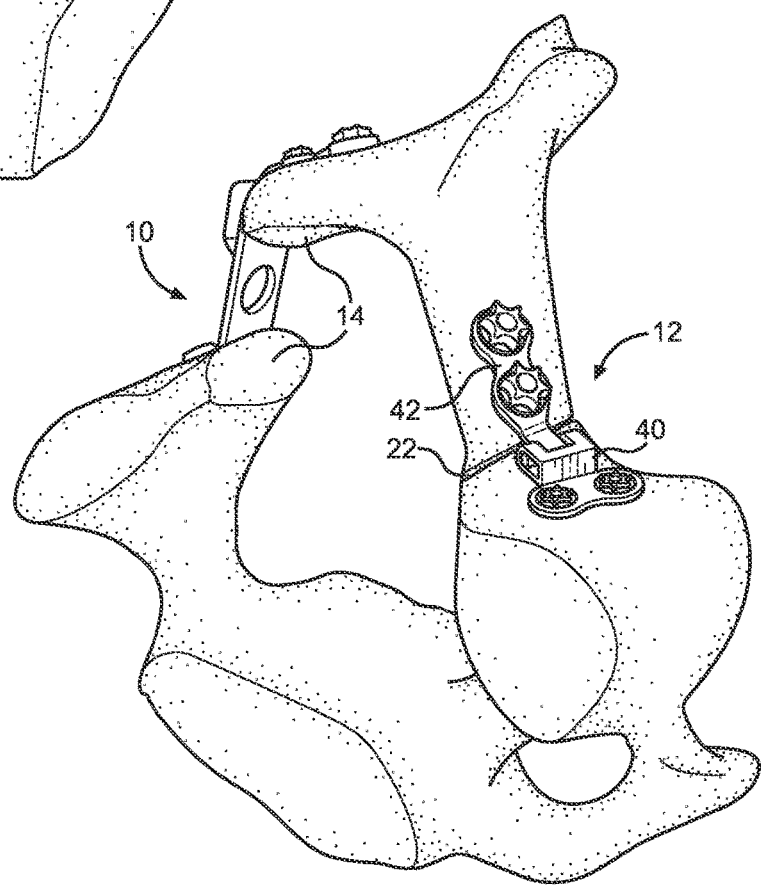

With initial reference to FIGS. 1-3, there is shown a device 10 and a device 12 as used for an open door laminoplasty procedure. The devices 10 and 12 are desirably configured to be adjustable in size and orientation so that they may be adapted to the site at the time of surgery.

In the open door laminoplasty procedure depicted, a cut 14 has been made completely through one side of a vertebrae 16 between a lamina 18 and a lateral mass 20 of the vertebrae 16. The device 10 spans the cut 14.

FIGS. 1 and 2 show the device 10 installed at the site of the cut 14 and fixed in place with fasteners. As seen, the device 10 is able to adjust in planar orientation or angular orientation or both to correspond to the structure of the lamina to be spanned at the site of the cut 14.

A second partial cut 22 has been made on the opposite lateral side, and the lamina 18 is hinged about the partial cut 22. The device 12 spans the cut 22.

FIGS. 1 and 3 show the device 12 installed at the site of the partial cut 22 and fixed in place with fasteners. As seen, the device 12 is able to adjust in planar orientation or angular orientation or both to correspond to the structure of the lamina to be spanned at the site of the cut 22.

Each of the devices 10 and 12 is advantageously configured to be able to adjust in planar orientation or angular orientation or both. The ability of the devices to adjust in its planar orientations, such as by being of adjustable planar orientation or angular orientation or both, enables the devices to be able to be provided in a variety of different configurations. This advantageously enables a reduction in the inventory of devices.

The ability to adjust the plan orientation enables the device to be adjusted to a variety of surgical sites. The ability to adjust the angular orientation of the device enables the device to be oriented to lie flush with on the lamina without having to bend the material of the device as is done conventionally. The devices 10 and 12 are of hinged construction and adjustable planar construction.

Figure 4:
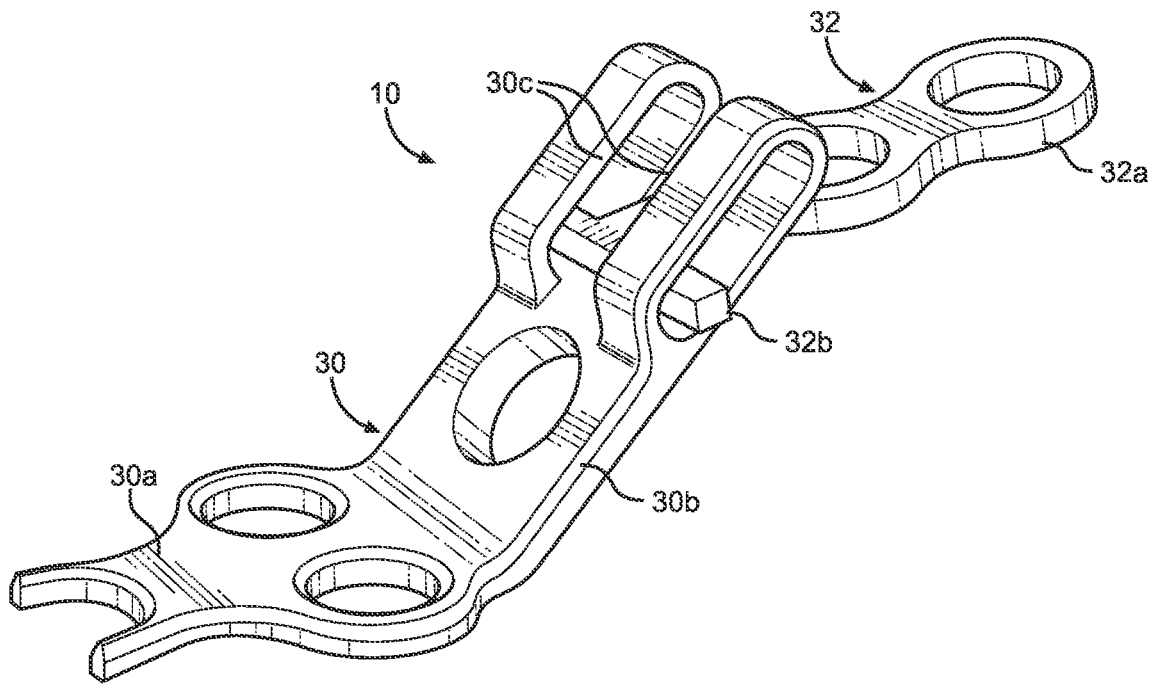
FIGS. 4-6 show the structure of one of the devices of FIGS. 1-3 designed for use at the location of a complete cut of the laminoplasty procedure.
Figure 5:
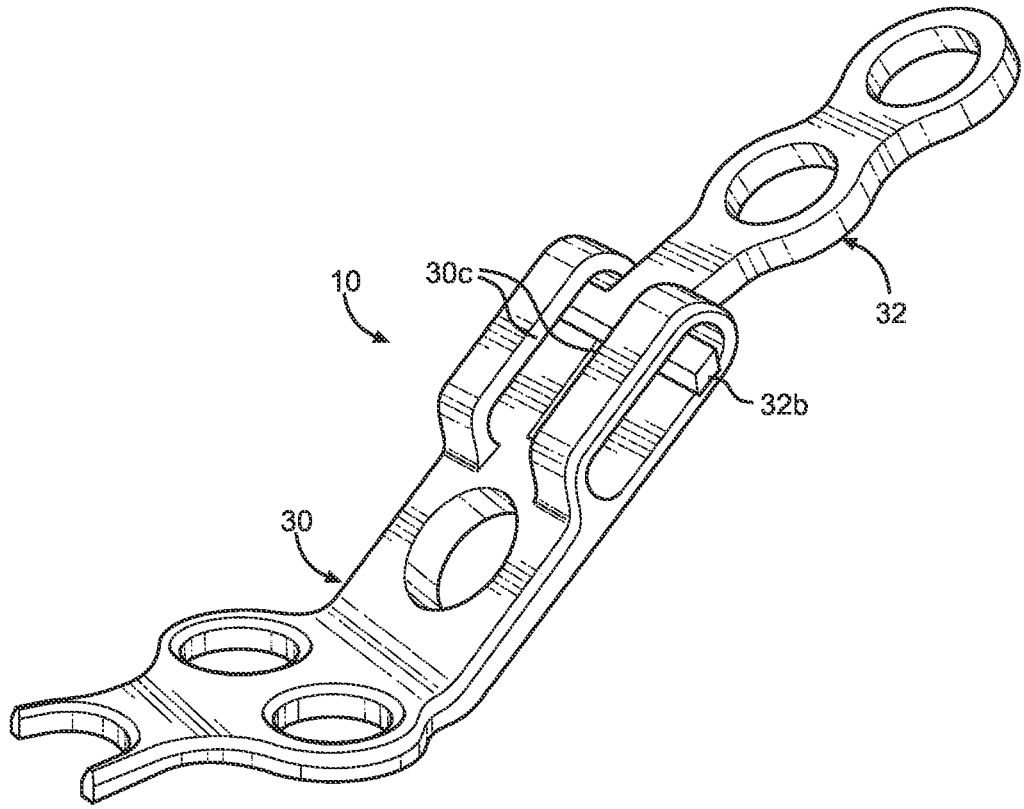
Figure 6:
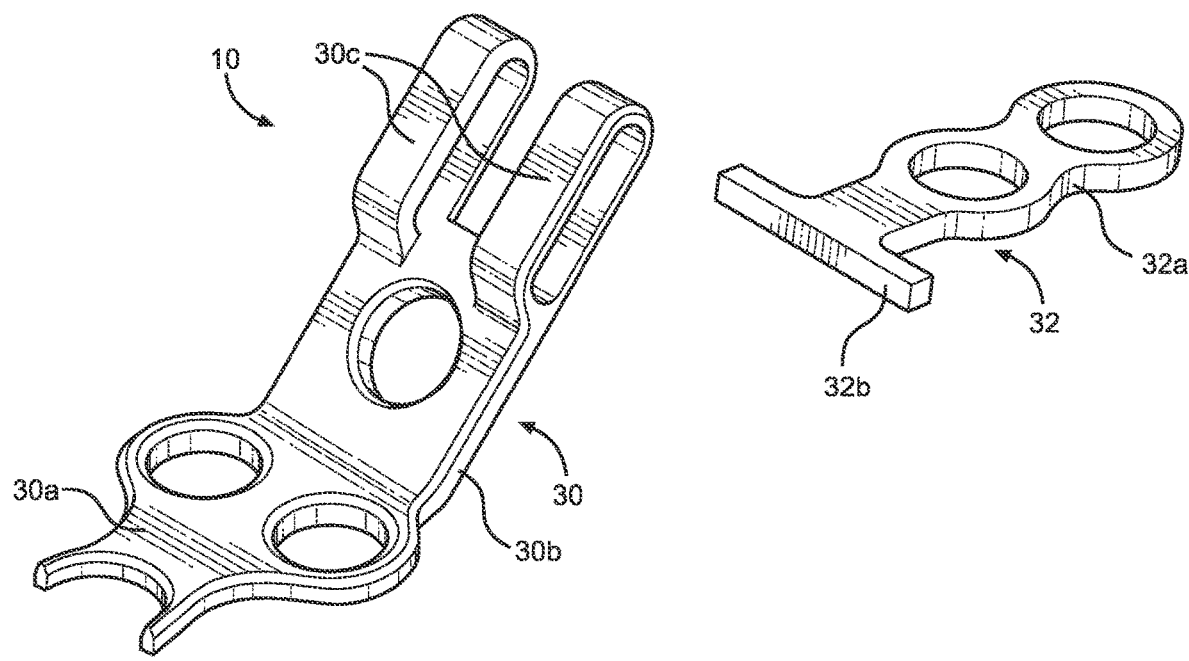

With additional reference to FIGS. 4-6, the device 10 includes a base 30 and an extension 32 hingedly and adjustably connected to the base 30 in a manner that enables adjustment of both the planar and the angular orientation of the device 10. As depicted, apertures are provided on the base 30 and the extension 32 for passage of fasteners to fasten the base and the extension 32 to the lamina.

The base 30 includes a seat 30*a* and a back 30*b* extending from the seat 30*a* in a reclined relationship, preferably at an angle of from about 30 to about 75 degrees, most preferably about 45 degrees. A pair of spaced apart and aligned slots 30*c* are located at the distal or free end of the back 30*b*.

The extension 32 is T-shaped and includes an elongated body 32*a* having a head 32*b* at an end of the body 32*a*, with the head 32*b* having oppositely extending arms of uniform length. The device 10 is assembled by placing the head 32*b* of the extension 32 to span between the slots 30*c* of the back 30*b* of the base 30. As depicted in FIG. 4, the head 32*b* is at a lowermost end of the slots 30*c*, and in FIG. 5 the head 32*b* is at an uppermost end of the slots 30*c*. These views depict the range of planar adjustment. In addition, FIGS. 4 and 5 depict different angular orientations of the head 32*b* relative to the extension 32, it being understood that the head 32*b* may freely pivot within the slots 30*c* to permit various relative angular orientations.

In this regard, the term slots as used herein will be understood to refer to the oval or elongate slots shown in the drawings and will be understood to encompass other elongate geometries or structures that can provide a constrained path for travel of the head of the extension that enables the head to pivot and to change position for adjustment of the planar orientation or the angular orientation or both of the implant device. Also, it will be appreciated that the base may be constructed with only a single slot or structure in which the head may engage and be pivotally and movably positionable relative to the base.

Figure 7:
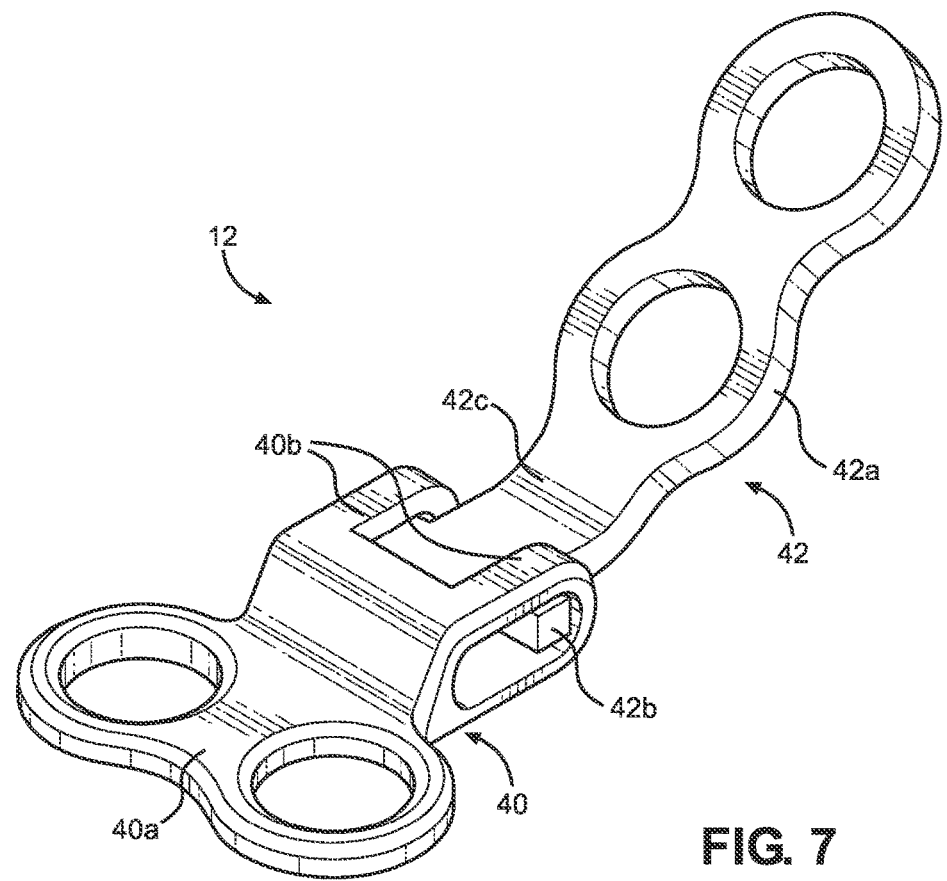
FIGS. 7-9 show one of the device of FIGS. 1-3 designed for use at the location of a partial cut of the laminoplasty procedure.
Figure 8:
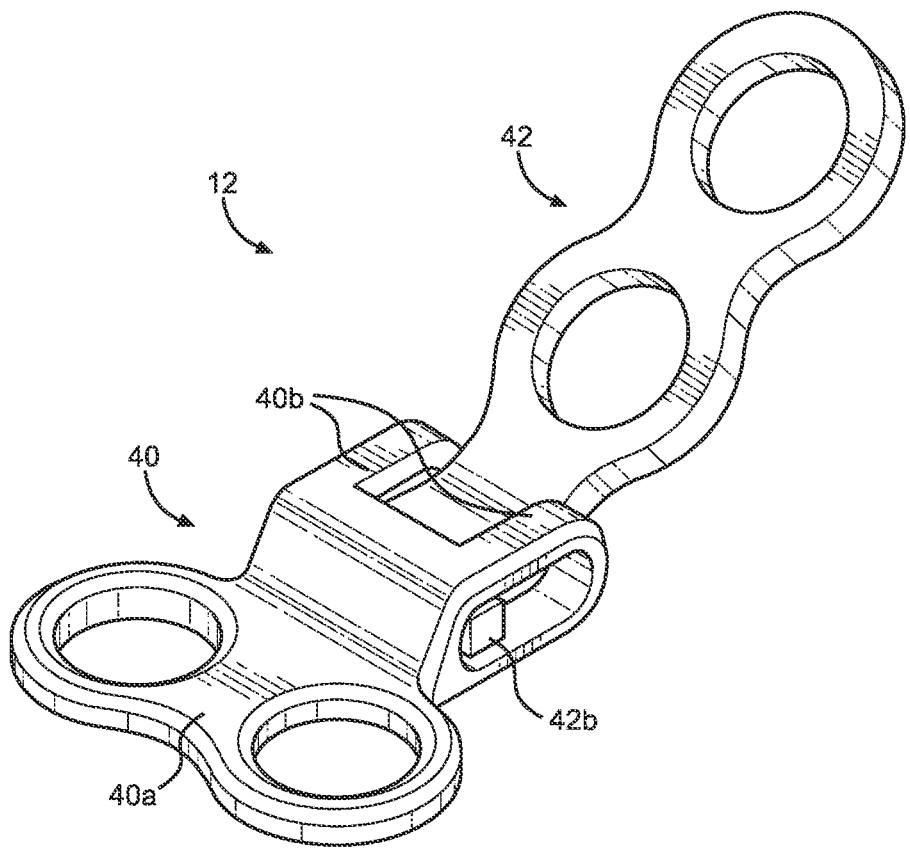
Figure 9:
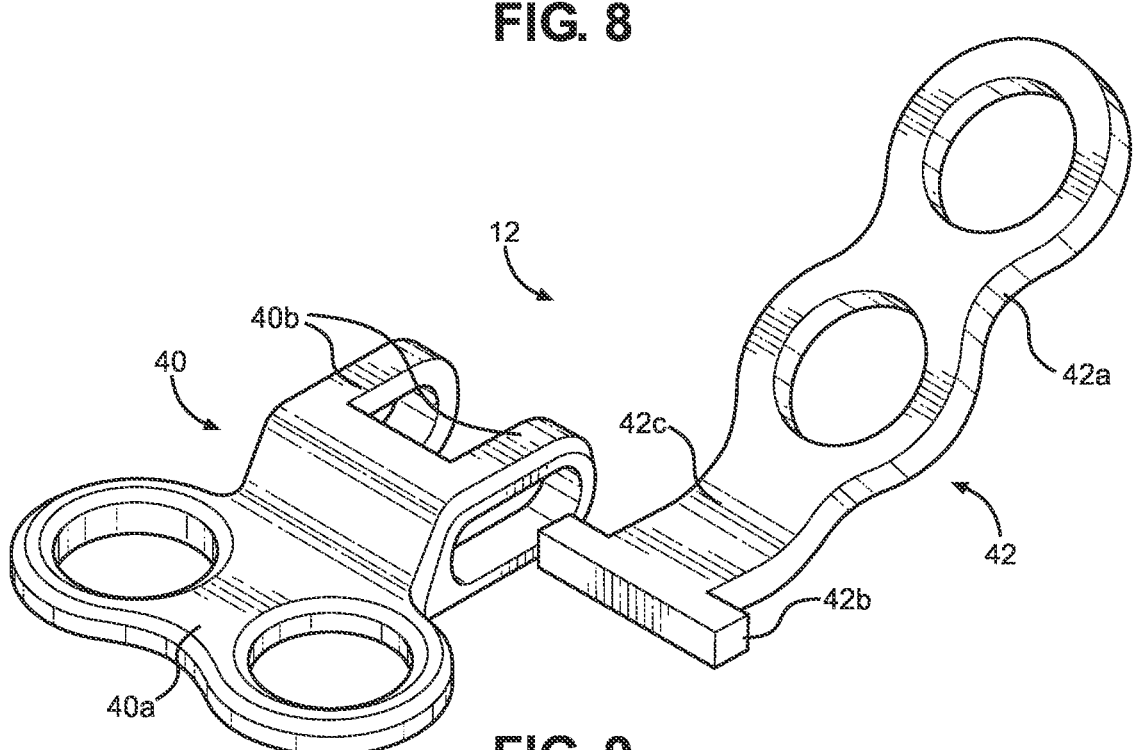

With additional reference to FIGS. 7-9, the device 12 includes a base 40 and an extension 42 adjustably connected to the base 40 in a manner that enables adjustment of both the planar or the angular orientation or both of the device 12. Apertures are provided on the base 40 and the extension 42 for passage of fasteners.

The base 40 includes a seat 40*a* and a pair of spaced apart and aligned ovals or slots 40*b* extending from the seat 40*a*.

The extension 42 is T-shaped and includes an elongated body 42*a* having a head 42*b* at an end of the body 42*a* with oppositely extending arms of uniform length. A bend 42*c* is provided between the body 42*a* and the head 42*b*. The bend 42*c* preferably disposes the head 42*b* at an angle relative to the body 42*a*, the angle being from about 10 to about 60 degrees, most preferably about 40 degrees.

The device 12 is assembled by placing the head 42*b* of the extension 42 to span between the slots 40*b* of the base 40. As depicted in FIG. 8, the head 42*b* is at a lowermost end of the slots 40*b*, and in FIG. 7 the head 42*b* is at an uppermost end of the slots 40*b*. These views depict the range of planar adjustment, in this case, length adjustment. In addition, FIGS. 7 and 8 depict different angular orientations of the head 42*b* relative to the extension 42, it being understood that the head 42*b* may freely pivot within the slots 40*b* to permit various relative angular orientations.

Figure 10:
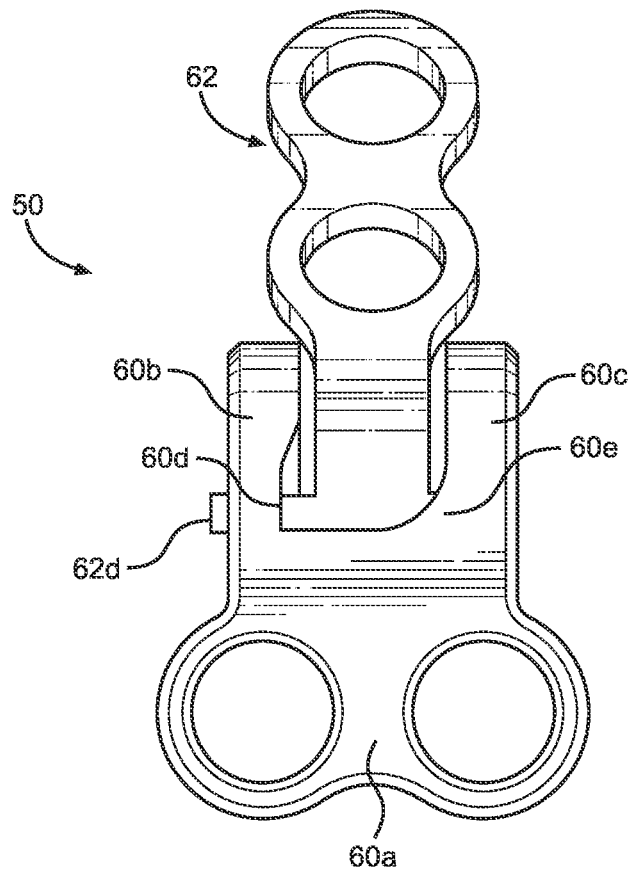
FIGS. 10-12 show an alternate embodiment of a device according the disclosure and designed for use at the location of a partial cut of the laminoplasty procedure.
Figure 11:
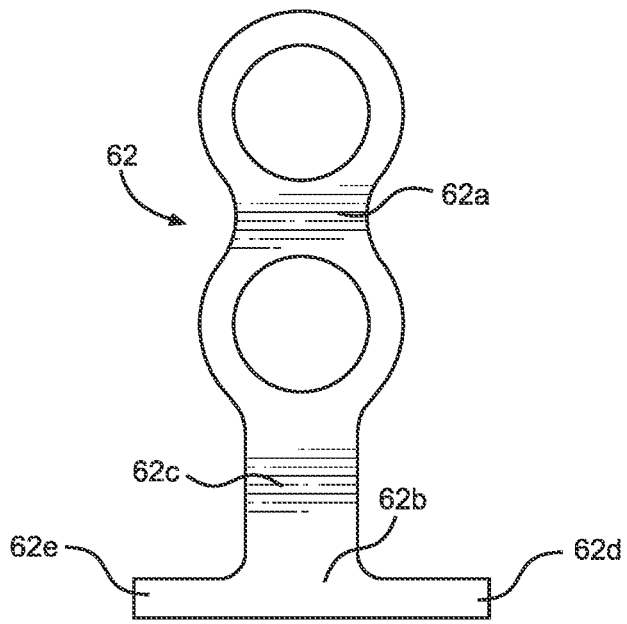
Figure 12:
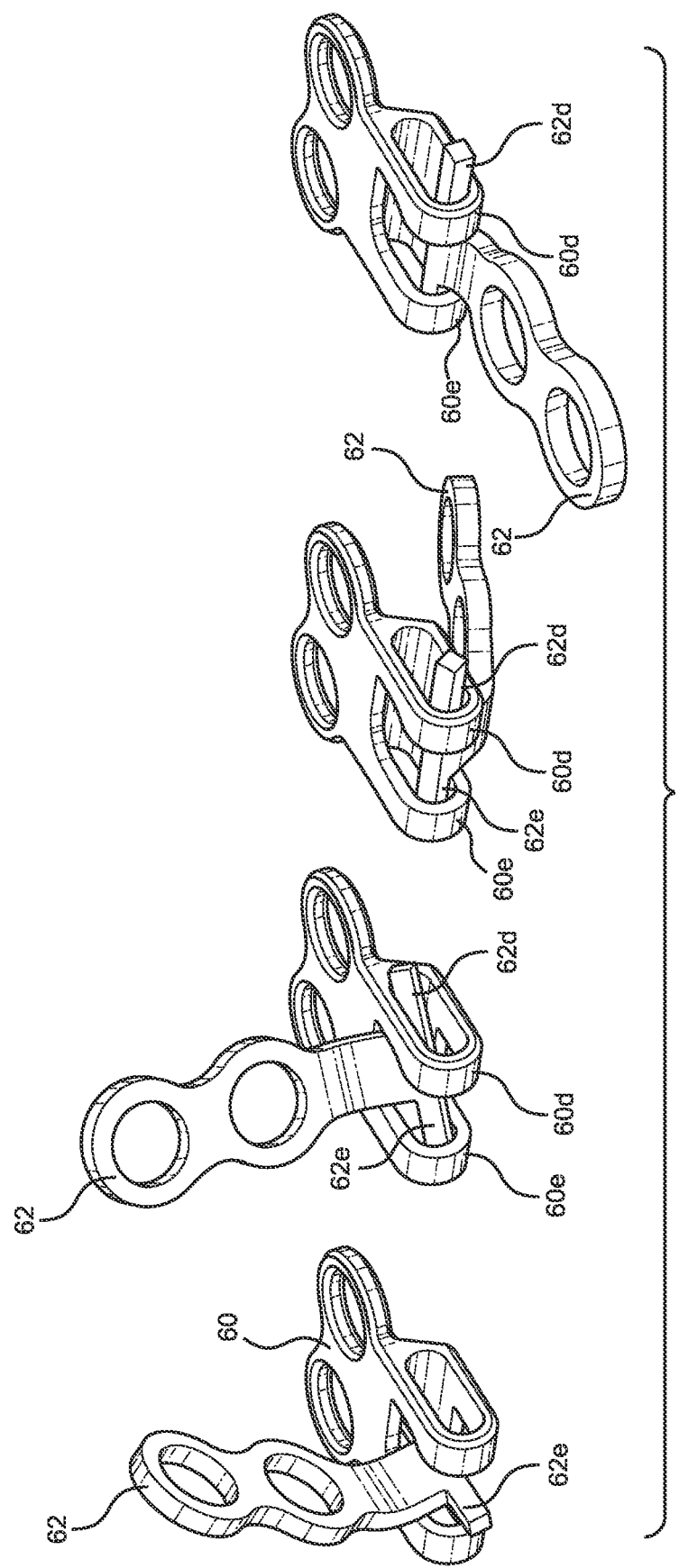
Figure 13:
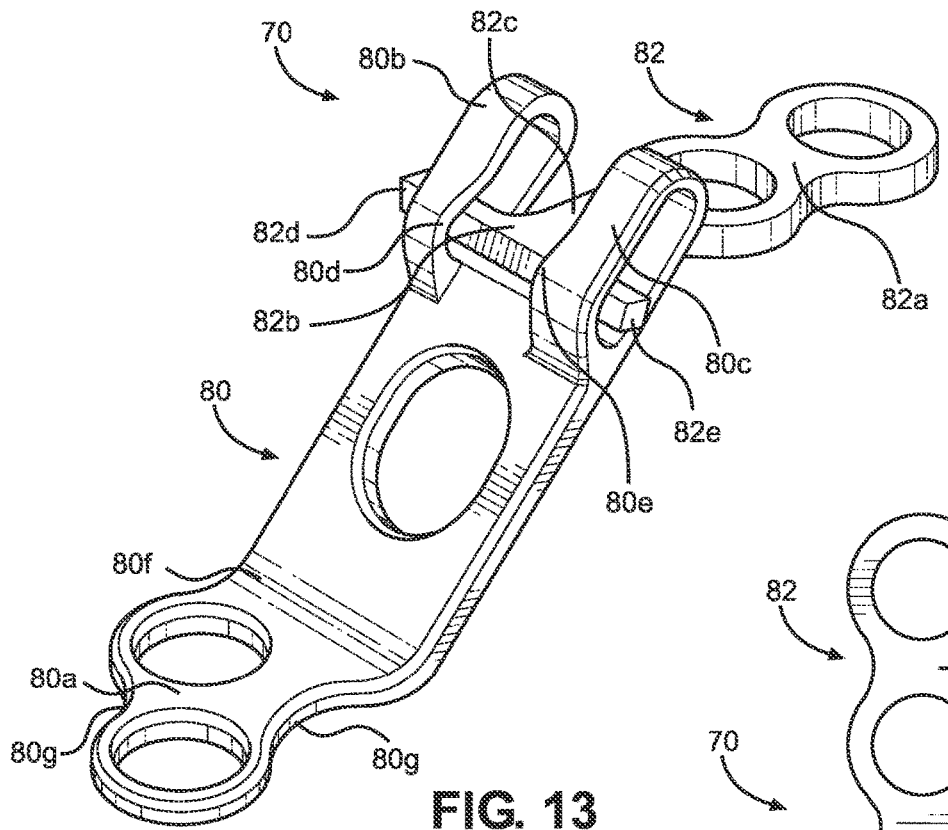
FIGS. 13-16 show an alternate embodiment of a device according the disclosure and designed for use at the location of a full cut of the laminoplasty procedure.

FIGS. 10-12 show an alternate embodiment of a device 50 according the disclosure and designed for use at the location of a partial cut of the laminoplasty procedure. The device 50 is similar to the device 12 and includes a base 60 and an extension 62 adjustably connected to the base 60 in a manner that enables adjustment of both the planar and the angular orientation of the device 50. However, the device 50 is advantageously constructed to resist undesired separation of the extension 62 from the base 60. Apertures are provided on the base 60 and the extension 62 for passage of fasteners.

The base 60 includes a seat 60*a* and a pair of spaced apart and aligned ovals or slots 60*b* and 60*c* extending from the seat 60*a*. A gap is defined by the spacing of the slots 60*a* and 60*b*. The slot 60*b* includes an indent 60*d* at the interior lower edge thereof. The slot 60*c* includes an enlarged interior lower edge thereof that provides a stop 60*e* that is opposite of the indent 60*d* and extends towards the indent 60*d*.

The extension 62 is T-shaped and includes an elongated body 62*a* having a head 62*b* at an end of the body 62*a*. A neck 62*c* is provided between the body 62*a* and the head 62*b*. The head 62*b* includes a pair of oppositely extending arms 62*d* and 62*e*. The arm 62*d* is longer than the arm 62*e*. As explained more fully below, the arms 62*d* and 62*e* cooperate with the indent 60*d* and the stop 60*e* to resist undesired separation of the extension 62 from the base 60.

Similar to that described for the device 12, it will be appreciated that the structure of the device 50 enables different angular orientations of the head 62b relative to the extension 62, it being understood that the head 62b may freely pivot within the slots 60b and 60c to permit various relative angular orientations.

With reference to FIG. 12, the device 50 is assembled by placing the head 62b of the extension 62 to span between the slots 60b and 60c of the base 60. The head 62b is inserted into a lowermost end of the slots 60b and 60C, with the shorter arm 62d inserted via the space provided by the indent 60d. The longer arm 62d of the head 62b is slid into the space of the indent 62d and the shorter arm 62e is located behind the stop 60e to complete installation. Thus, to remove the extension 62 from the base 60, one has to reverse the insertion process, which takes specific manipulation of the arms 62d and 62e relative to the indent 60d and the stop 60e. These manipulations are unlikely to occur once the implant 50 is installed in a patient. Thus, it will be appreciated that the arms 62d and 62e cooperate with the indent 60d and the stop 60e to resist undesired separation of the extension 62 from the base 60.

FIGS. 13-16 show an alternate embodiment of a device 70 according the disclosure and designed for use at the location of a full cut of the laminoplasty procedure.

The device 70 is similar to the device 10 and includes a base 80 and an extension 82 adjustably connected to the base 80 in a manner that enables adjustment of both the planar and the angular orientation of the device 70. However, the device 70 is advantageously constructed to resist undesired separation of the extension 82 from the base 80 and to enable a desired placement of bone screws. Apertures are provided on the base 80 and the extension 82 for passage of fasteners.

The base 80 includes a seat 80a and a pair of spaced apart and aligned ovals or slots 80b and 80c extending from the seat 80a. A gap is defined by the spacing of the slots 80a and 80b. The slot 80b includes an indent 80d at the interior lower edge thereof. The slot 80c includes an enlarged interior lower edge thereof that provides a stop 80e that is opposite of the indent 80d and extends towards the indent 80d.

Figure 14:
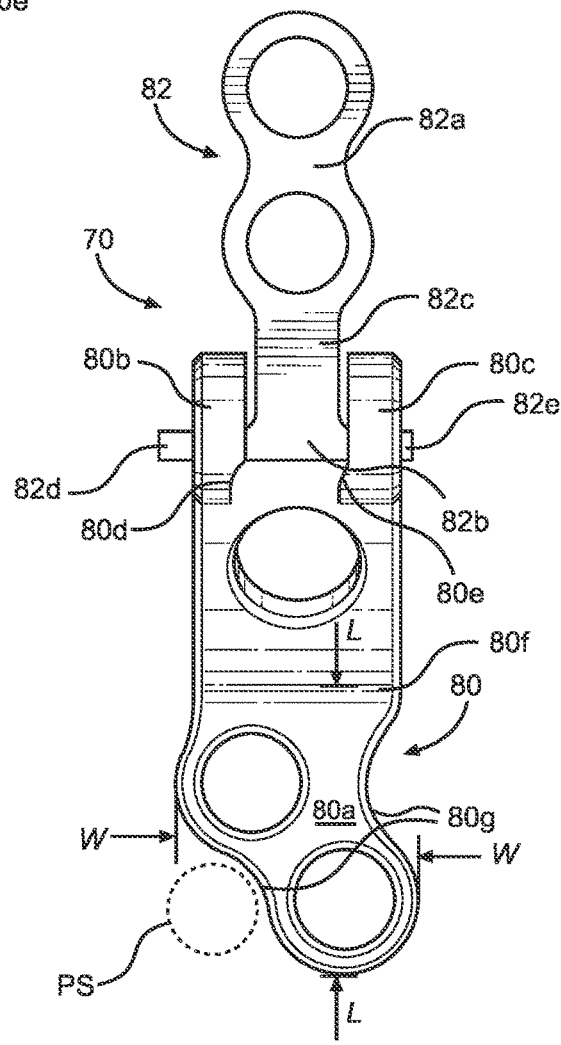
Figure 15:
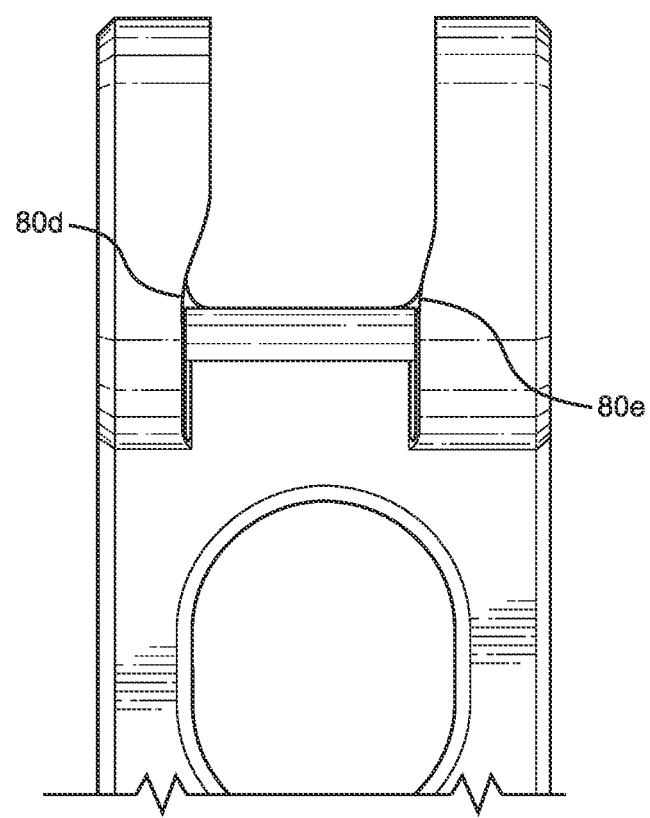

As shown in FIG. 14, the seat 80a is also advantageously configured to minimize the width dimension, noted by arrows W, and the planar dimension, in this case length dimension, noted by the arrows L, representing the length of the seat 80a that is seated on the spine, which is from a bend 80f to a distal end of the seat 80. This configuration of the seat 80a provides concave indents 80g that provide locations to enable fasteners in the nature of bone screws, such as a pedicle screw PS or lateral mass screw or the like to be placed immediately adjacent the base 80a.

The extension 82 is T-shaped and includes an elongated body 82a having a head 82b at an end of the body 82a. A neck 82c is provided between the body 82a and the head 82b. The head 82b includes a pair of oppositely extending arms 82d and 82e. The arm 82d is longer than the arm 82e. The arms 82d and 82e cooperate with the indent 80d and the stop 80e to resist undesired separation of the extension 82 from the base 80.

Similar to that described for the device 10, it will be appreciated that the structure of the device 70 enables different angular orientations of the head 82b relative to the extension 82, it being understood that the head 82b may freely pivot within the slots 80b and 80c to permit various relative angular orientations.

Figure 16:
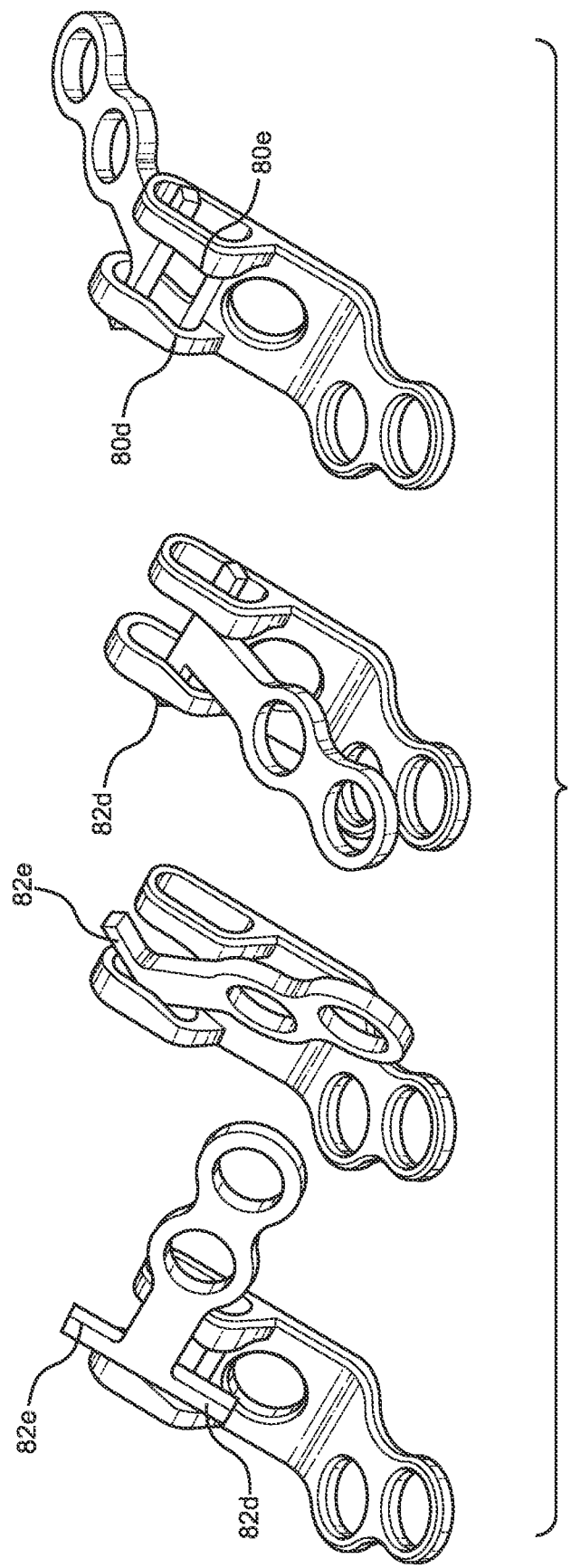

With reference to FIG. 16, the device 70 is assembled by placing the head 82b of the extension 82 to span between the slots 80b and 80c of the base 80. The head 82b is inserted into a lowermost end of the slots 80b and 80C. The longer arm 82d of the head 82b is slid into the space of the indent 82d and the shorter arm 82e is located behind the stop 80e to complete installation. Thus, to remove the extension 82 from the base 80, one has to reverse the insertion process, which takes specific manipulation of the arms 82d and 82e relative to the indent 80d and the stop 80e. These manipulations are unlikely to occur once the implant 70 is installed in a patient. Thus, it will be appreciated that the arms 82d and 82e cooperate with the indent 80d and the stop 80e to resist undesired separation of the extension 82 from the base 80.

Figure 17:
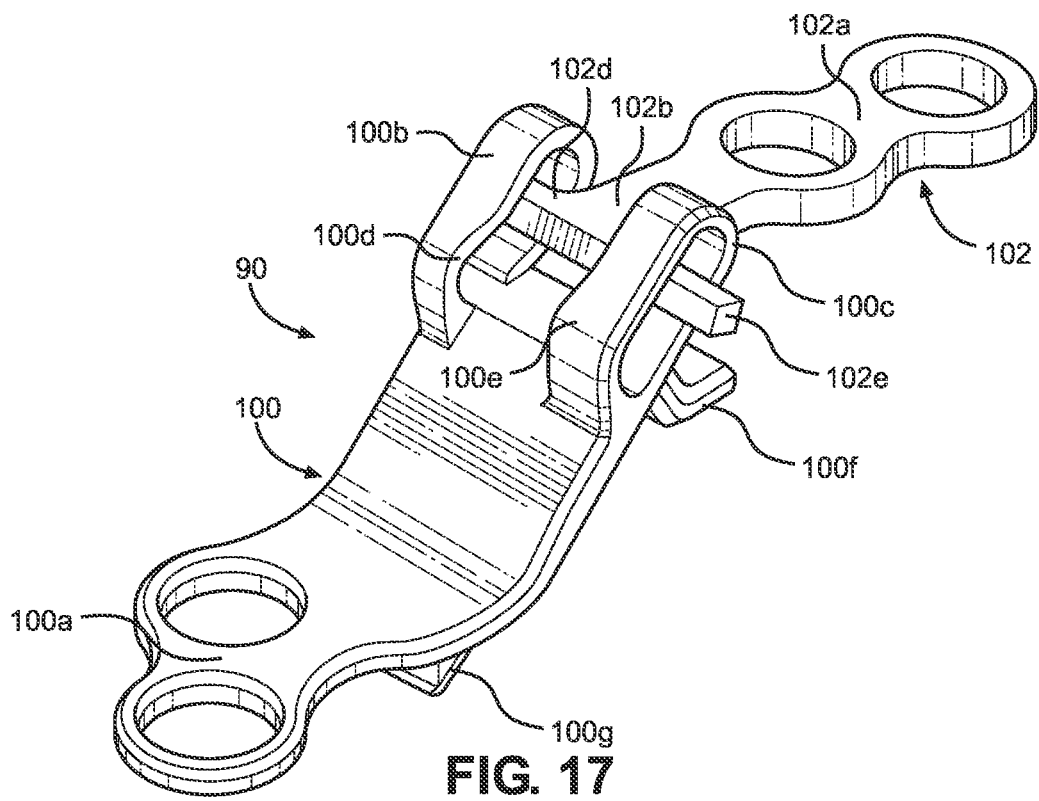
FIGS. 17-19 show an additional embodiment of a device according the disclosure and designed for use at the location of a full cut of the laminoplasty procedure.
Figure 18:
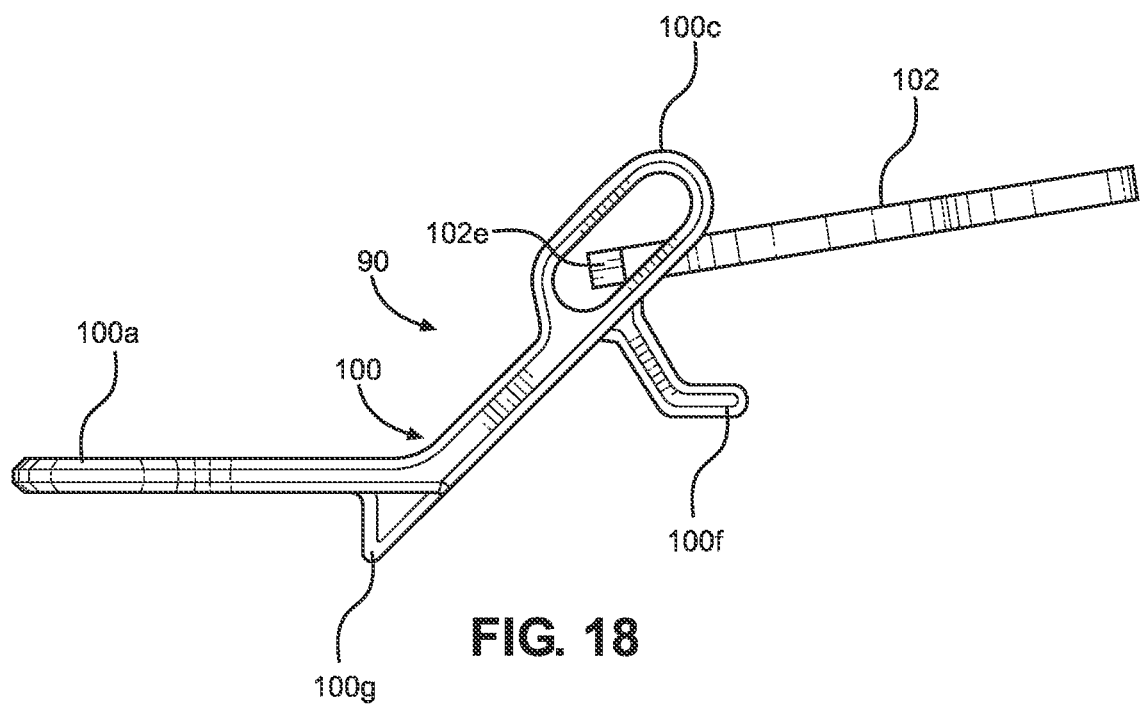
Figure 19:
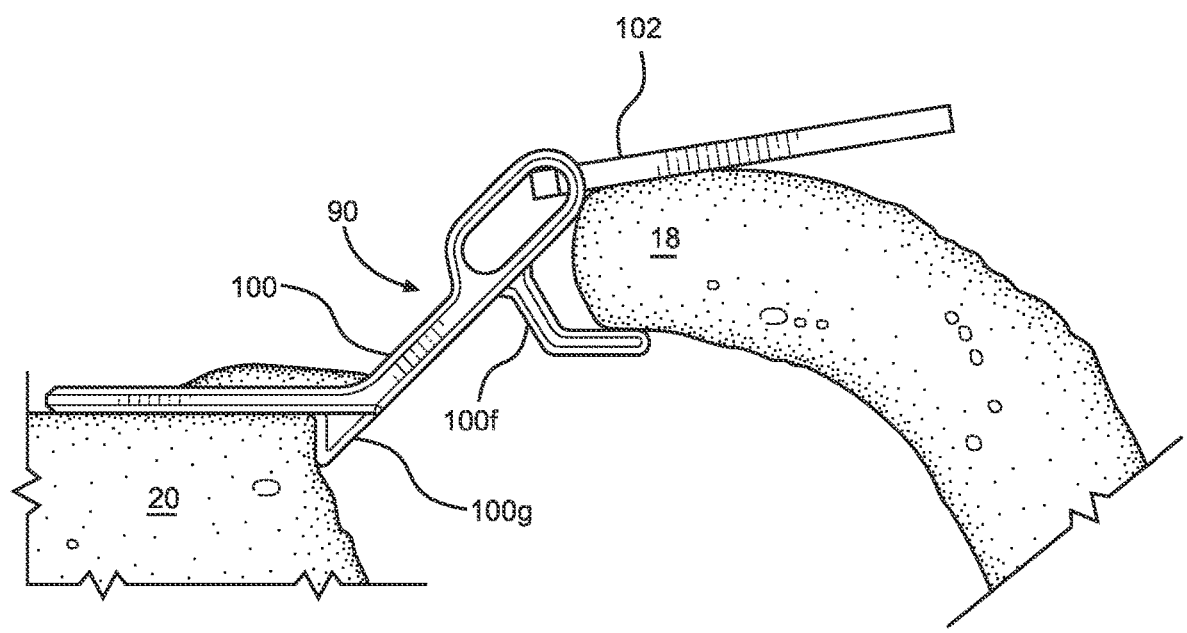

FIGS. 17-19 show an additional embodiment of a device 90 according the disclosure and designed for use at the location of a full cut of the laminoplasty procedure.

The device 90 is similar to the device 70 and includes a base 100 and an extension 102 adjustably connected to the base 100 in a manner that enables adjustment of the planar orientation or the angular orientation or both of the device 90.

As in the case of the device 70, the device 90 is advantageously constructed to resist undesired separation of the extension 102 from the base 100 and to enable a desired placement of bone screws. Apertures are provided on the base 100 and the extension 102 for passage of fasteners.

The base 100 includes a seat 100a and a pair of spaced apart and aligned ovals or slots 100b and 100c extending from the seat 100a. A gap is defined by the spacing of the slots 100a and 100b. The slot 100b includes an indent 100d at the interior lower edge thereof. The slot 100c includes an enlarged interior lower edge thereof that provides a stop 100e that is opposite of the indent 100d and extends towards the indent 100d.

Additional features of the base 100 include a hook 100f and a foot 100g integrally formed therewith. As shown in FIG. 19, the hook 100f enables the base 100 to engage and hook to the lamina 18 of the vertebrae 16, and the foot 100g buttresses against the lateral mass 20 of the vertebrae 16.

The extension 102 is T-shaped and includes an elongated body 102a having a head 102b at an end of the body 102a. A neck 102c is provided between the body 102a and the head 102b. The head 102b includes a pair of oppositely extending arms 102d and 102e. The arm 102d is longer than the arm 102e. The arms 102d and 102e cooperate with the indent 100d and the stop 100e to resist undesired separation of the extension 102 from the base 100.

As in the case of the device 70, the device 90 enables different angular orientations of the head 102b relative to the extension 102, it being understood that the head 102b may freely pivot within the slots 100b and 100c to permit various relative angular orientations. In addition to the benefits of this previously described, this angular adjustability feature in combination with the additional hook 100f and 100g structures of the base 100 advantageously enables the device 90 to accommodate a variety of lamina thicknesses. In this regard, once the device 90 is installed onto the vertebrae, the ability of the extension 102 to pivot enables the device 90 to contour to the lamina regardless of the thickness of the lamina 20 or the angle to be spanned.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure

The invention claimed is:

1. A surgical implant device configured to be adjustable in size and orientation so as to be adaptable to a surgical site, the implant device, comprising:
   a base and an extension adjustably connectable to the base to enable adjustment of both planar and angular orientations of the surgical implant device,
   the base having a seat and a back having a length axis and extending from the seat, and a pair of spaced apart and aligned elongate slots located at a distal end of the back of the base, the elongate slots having length axes that are located along and aligned with the length axis of the back, and
   the extension having an elongated body with a head at an end of the elongated body of the extension, the head having oppositely extending arms, the head of the elongated body of the extension being positionable between the slots of the base so that the arms of the head of the elongated body span between the slots of the back of the base,
   wherein when the head of the extension is positioned between the slots of the base when the implant device is installed in a patient during surgery, the head of the extension is freely pivotable within the slots of the base to permit a plurality of angular orientations of the implant device and the head is movable along the elongate length of the slots to provide adjustable planar orientation of the implant device based on the location of the head along the elongate length of the slots.

2. The device of claim 1, wherein the device is configured for use at complete cut or a partial cut location of an open door laminoplasty surgical site.

3. The device of claim 1, wherein one of the oppositely extending arms of the head of the extension is longer than the other one of the arms.

4. The device of claim 3, wherein one of the slots of the base defines an indent and one of the slots defines a stop opposite the indent, wherein when the extension is connected to the base, the longer one of the arms of the head of the extension is positioned within the slot having the indent and the shorter arm of the head is positioned within the slot having the stop and the arms cooperate with the indent and the stop to resist separation of the extension from the base.

5. The device of claim 1, wherein the seat of the base is configured to minimize a width dimension of the base and a length dimension of the base, the seat shaped to define concave indents along opposite sides thereof, the concave indents defining locations along the sides of the seat to enable bone screws to be placed immediately adjacent to the seat of the base.

6. The device of claim 1, wherein the base further includes a hook and a foot integrally formed therewith and extending from spaced apart locations of a lower surface of the base.

7. A surgical implant device configured to be adjustable in size and orientation so as to be adaptable to a surgical site, the implant device, comprising:
   a one-piece base and an extension adjustably connectable to the base to enable adjustment of both planar and angular orientation of the surgical implant device;
   the base having a seat, a back extending from the seat, and a pair of spaced apart and aligned elongate slots located at a distal end of the back of the base; and
   the extension having an elongated body with a head at an end of the elongated body of the extension, the head being pivotally or movably mountable or both to the extension to permit a plurality of different configurations of the implant device and including oppositely extending arms each positionable in one of the elongate slots of the base to pivotally and movably mount the head to the base.

8. The device of claim 7, wherein the back of the base includes an elongate slot and the head is positionable within the elongate slot to pivotally and movably mount the head to the base.

9. The device of claim 7, wherein the seat of the base is configured to minimize a width dimension of the base and a length dimension of the base, the seat shaped to define concave indents along opposite sides thereof, the concave indents defining locations along the sides of the seat to enable bone screws to be placed immediately adjacent to the seat of the base.

10. The device of claim 7, wherein the base further includes a hook and a foot integrally formed therewith and extending from spaced apart locations of a lower surface of the base.

11. The device of claim 7, wherein the different configurations of the surgical implant device comprise different planar or angular orientations or both of the surgical implant device.

12. A surgical implant device configured for use at complete cut location of an open door laminoplasty surgical site to span between a lamina of a vertebrae and an open mass of a vertebrae, the implant device configured to be adjustable in size and orientation so as to be adaptable to the open door laminoplasty surgical site at the time of surgery, the implant device, comprising:
   a base and an extension adjustably connected to the base to enable adjustment of planar orientation or angular orientation or both of the surgical implant device,
   the base having a seat and a back having a length axis and extending from the seat in a reclined relationship, a pair of spaced apart and aligned elongate slots located at a distal end of the back of the base, the elongate slots having aligned length axes that are located along and aligned with the length axis of the back, a hook configured to be able to hook onto the lamina of the vertebrae and a foot configured to be able to be able to buttress against the lateral mass of the vertebrae, and
   the extension having an elongated body with a head at an end of the elongated body of the extension, the head having oppositely extending arms, the head of the elongated body of the extension being positionable between the slots of the base so that the arms of the head of the elongated body span between the slots of the back of the base,
   wherein when the head of the extension is positioned between the slots of the base when the implant device is installed in a patient during surgery, the head of the extension is freely pivotable within the slots of the base to permit a plurality of angular orientations of the implant device and the head is movable along the elongate length of the slots to provide adjustment of the planar orientation of the implant device based on the location of the head along the elongate length of the slots.

13. A surgical implant device configured for use at complete cut location of an open door laminoplasty surgical site to span between a lamina of a vertebrae and an open mass of a vertebrae, the surgical implant device configured to be adjustable in size and orientation so as to be adaptable to the open door laminoplasty surgical site at the time of surgery, the surgical implant device, comprising:
- a one-piece base and a one-piece extension adjustably connected to the base to enable adjustment of both length and angular orientation of the surgical implant device,
- the base having a seat and a back having a length axis and extending from the seat in a reclined relationship, a pair of spaced apart and aligned elongate slots located at a distal end of the back of the base, the elongate slots having aligned length axes that are located along and aligned with the length axis of the back, a hook configured to be able to hook onto the lamina of the vertebrae and a foot configured to be able to be able to buttress against the lateral mass of the vertebrae, and
- the extension having an elongated body with a head at an end of the elongated body of the extension, the head having oppositely extending arms, the head of the elongated body of the extension being positionable between the slots of the base so that the arms of the head of the elongated body span between the slots of the back of the base,
- wherein when the head of the extension is positioned between the slots of the base when the surgical implant device is installed in a patient during surgery, the head of the extension is freely pivotable within the slots of the base to permit a plurality of angular orientations of the surgical implant device and the head is movable along the elongate length of the slots to provide adjustable length of the surgical implant device based on the location of the head along the elongate length of the slots.

* * * * *